US008911763B2

(12) United States Patent
Geistlich et al.

(10) Patent No.: US 8,911,763 B2
(45) Date of Patent: Dec. 16, 2014

(54) COLLAGEN CARRIER OF THERAPEUTIC GENETIC MATERIAL AND METHOD

(75) Inventors: Peter Geistlich, Stansstad (CH); Lothar Schloesser, Darmstadt (DE)

(73) Assignee: Ed. Geistlich Soehne AG fuer Chemistrie Industrie, Wolhusen (CH)

( * ) Notice: Subject to any disclaimer, the term of this patent is extended or adjusted under 35 U.S.C. 154(b) by 341 days.

(21) Appl. No.: 11/928,384

(22) Filed: Oct. 30, 2007

(65) Prior Publication Data

US 2008/0107710 A1    May 8, 2008

Related U.S. Application Data

(63) Continuation of application No. 11/046,897, filed on Feb. 1, 2005, now abandoned, which is a continuation-in-part of application No. 10/213,437, filed on Aug. 7, 2002, now abandoned, said application No. 11/046,897 is a continuation-in-part of application No. 09/925,728, filed on Aug. 10, 2001, now Pat. No. 7,141,072, and a continuation-in-part of application No. 09/545,465, filed on Apr. 7, 2000, now Pat. No. 6,752,834, said application No. 11/046,897 is a continuation-in-part of application No. 10/869,909, filed on Jun. 18, 2004, now abandoned, which is a continuation of application No. 09/545,465, which is a continuation-in-part of application No. PCT/GB98/02976, filed on Oct. 5, 1998.

(60) Provisional application No. 60/311,078, filed on Aug. 10, 2001, provisional application No. 60/224,010, filed on Aug. 10, 2000.

(30) Foreign Application Priority Data

Oct. 10, 1997    (GB) .................................... 9721585.9

(51) Int. Cl.

| A61F 2/00 | (2006.01) |
|---|---|
| A61F 2/06 | (2013.01) |
| A61K 48/00 | (2006.01) |
| A61F 2/30 | (2006.01) |
| A61L 15/32 | (2006.01) |
| A61L 27/20 | (2006.01) |
| A61K 38/18 | (2006.01) |
| A61L 27/38 | (2006.01) |
| A61L 27/54 | (2006.01) |
| A61L 31/16 | (2006.01) |
| A61L 31/14 | (2006.01) |
| A61L 15/40 | (2006.01) |
| A61L 31/00 | (2006.01) |
| A61L 31/04 | (2006.01) |
| A61L 27/36 | (2006.01) |
| A61L 27/24 | (2006.01) |
| A61F 2/28 | (2006.01) |
| A61B 17/00 | (2006.01) |
| A61F 2/46 | (2006.01) |
| A61K 9/70 | (2006.01) |
| A61B 17/06 | (2006.01) |
| A61K 9/00 | (2006.01) |

(52) U.S. Cl.
CPC ............. *A61L 31/16* (2013.01); *A61F 2/30756* (2013.01); *A61F 2002/0086* (2013.01); *A61F 2002/30677* (2013.01); *A61F 2002/30062* (2013.01); *A61F 2002/2817* (2013.01); *A61L 15/325* (2013.01); *A61L 27/20* (2013.01); *A61K 38/1875* (2013.01); *A61F 2/28* (2013.01); *A61L 27/3847* (2013.01); *A61F 2/30767* (2013.01); *A61L 27/54* (2013.01); *A61B 17/00234* (2013.01); *A61K 48/0075* (2013.01); *A61F 2002/4635* (2013.01); *A61L 31/14* (2013.01); *A61F 2002/3093* (2013.01); *A61F 2310/00365* (2013.01); *A61F 2002/009* (2013.01); *A61F 2310/00982* (2013.01); *A61L 15/40* (2013.01); *A61F 2002/30932* (2013.01); *A61F 2240/001* (2013.01); *A61F 2002/30971* (2013.01); *A61B 17/00491* (2013.01); *A61L 2300/258* (2013.01); *A61L 31/005* (2013.01); *A61K 9/7023* (2013.01); *A61L 31/044* (2013.01); *A61F 2/0077* (2013.01); *A61L 27/36* (2013.01); *A61L 2430/06* (2013.01); *A61L 2300/414* (2013.01); *A61F 2210/0004* (2013.01); *A61B 17/06166* (2013.01); *A61K 9/0024* (2013.01); *A61L 27/24* (2013.01); *A61F 2002/30761* (2013.01); *A61L 27/3852* (2013.01)
USPC .......................... 424/425; 623/1.47; 514/44 R

(58) Field of Classification Search
USPC .......................... 623/1.47; 424/425; 514/44 R
See application file for complete search history.

(56) References Cited

U.S. PATENT DOCUMENTS

| 4,394,370 A | 7/1983 | Jefferies |
|---|---|---|
| 4,488,911 A | 12/1984 | Luck et al. |

(Continued)

FOREIGN PATENT DOCUMENTS

| AU | 660045 | 6/1995 |
|---|---|---|
| AU | 663150 | 9/1995 |

(Continued)

OTHER PUBLICATIONS

J. Fang et al.: "Stimulation of New Bone Formation by Direct Transfer of Osteogenic Plasmid Genes," Proc. Natl. Acad. Sci. USA, 1996, vol. 93, No. 12, pp. 5753-5758.

(Continued)

*Primary Examiner* — Marcia S Noble
(74) *Attorney, Agent, or Firm* — Rothwell, Figg, Ernst & Manbeck, P.C.

(57) ABSTRACT

A collagen matrix material is charged with a cell growth-promoting derived nucleic acid sequence. The nucleic acid sequence-charged collagen matrix material may be utilized in a method of promoting regeneration of surface cartilage of a joint. In the method, an area of injury is covered with the nucleic acid sequence-charged collagen matrix material, the collagen matrix material is fixed over the area to be treated, and the area is allowed to heal.

12 Claims, 4 Drawing Sheets

(56) References Cited

U.S. PATENT DOCUMENTS

| | | | |
|---|---|---|---|
| 4,505,266 A | | 3/1985 | Yannas et al. |
| 4,516,276 A | | 5/1985 | Mittelmeier et al. |
| 4,880,429 A | | 11/1989 | Stone |
| 4,975,527 A | | 12/1990 | Koezuka et al. |
| 5,162,430 A | | 11/1992 | Rhee et al. |
| 5,167,961 A | | 12/1992 | Lussi et al. |
| 5,197,985 A | | 3/1993 | Caplan et al. |
| 5,206,023 A | | 4/1993 | Hunziker |
| 5,254,133 A | | 10/1993 | Seid |
| 5,306,302 A | | 4/1994 | Bauer et al. |
| 5,306,311 A | | 4/1994 | Stone et al. |
| 5,413,597 A | | 5/1995 | Krajicek |
| 5,417,975 A | | 5/1995 | Lussi et al. |
| 5,523,348 A | | 6/1996 | Rhee et al. |
| 5,541,295 A | | 7/1996 | Barrach et al. |
| 5,567,806 A | | 10/1996 | Abdul-Malak et al. |
| 5,573,771 A | | 11/1996 | Geistlich et al. |
| 5,624,463 A | | 4/1997 | Stone et al. |
| 5,759,190 A | | 6/1998 | Vibe-Hanson et al. |
| 5,763,416 A | * | 6/1998 | Bonadio et al. ............. 514/44 R |
| 5,830,493 A | | 11/1998 | Yokota et al. |
| 5,837,278 A | | 11/1998 | Geistlich et al. |
| 5,842,477 A | | 12/1998 | Naughton et al. |
| 5,891,558 A | | 4/1999 | Bell et al. |
| 5,942,496 A | | 8/1999 | Bonadio et al. |
| 5,965,125 A | | 10/1999 | Mineau-Hanschke |
| 5,989,269 A | | 11/1999 | Vibe-Hansen et al. |
| 6,120,514 A | | 9/2000 | Vibe-Hansen et al. |
| 6,153,292 A | | 11/2000 | Bell et al. |
| 6,165,785 A | | 12/2000 | Ogle et al. |
| 6,221,109 B1 | | 4/2001 | Geistlich et al. |
| 6,283,980 B1 | | 9/2001 | Vibe-Hansen et al. |
| 6,352,558 B1 | | 3/2002 | Spector |
| 6,576,015 B2 | | 6/2003 | Geistlich et al. |
| 6,676,969 B2 | | 1/2004 | Geistlich et al. |
| 6,713,085 B2 | | 3/2004 | Geistlich et al. |
| 6,752,834 B2 | | 6/2004 | Geistlich et al. |
| 6,863,900 B2 | | 3/2005 | Kadiyala et al. |
| 7,141,072 B2 | | 11/2006 | Geistlich et al. |
| 2001/0016772 A1 | | 8/2001 | Lee et al. |
| 2002/0013626 A1 | | 1/2002 | Geistlich et al. |

FOREIGN PATENT DOCUMENTS

| | | | | |
|---|---|---|---|---|
| CA | | 2248327 | 9/1997 | |
| CA | WO 99/19005 | | * 4/1999 | ............. A61L 31/00 |
| DE | | 38 10803 A1 | 10/1989 | |
| DE | | 196 54 884 A1 | 9/1997 | |
| EP | | 0171176 A2 | 2/1986 | |
| FR | | 2679778 | 2/1993 | |
| JP | | 58058041 | 4/1983 | |
| JP | | 2033388 | 2/1990 | |
| JP | | 4226669 A | 8/1992 | |
| JP | | 10-216214 A | 8/1998 | |
| JP | | 2001-333974 | 4/2001 | |
| WO | WO 83/04177 A1 | | 12/1983 | |
| WO | WO 86/07265 | | 12/1986 | |
| WO | WO 90/05755 A1 | | 5/1990 | |
| WO | WO 90/13302 A1 | | 11/1990 | |
| WO | WO 92/13565 A1 | | 8/1992 | |
| WO | WO 93/10722 A2 | | 6/1993 | |
| WO | WO 93/11723 A1 | | 6/1993 | |
| WO | WO 93/19168 A1 | | 9/1993 | |
| WO | WO 95/18638 A1 | | 7/1995 | |
| WO | | 96/10426 A1 | 4/1996 | |
| WO | WO 96/24310 A1 | | 8/1996 | |
| WO | WO 96/25961 A1 | | 8/1996 | |
| WO | WO 97/32616 A1 | | 9/1997 | |
| WO | | 9738729 A1 | 10/1997 | |
| WO | WO 98/02976 A1 | | 1/1998 | |
| WO | WO 98/08469 A2 | | 3/1998 | |
| WO | WO 99/11664 A1 | | 3/1999 | |
| WO | | 9919005 A1 | 4/1999 | |
| WO | WO 00/74741 A2 | | 12/2000 | |
| WO | WO 01/08714 A1 | | 2/2001 | |
| WO | WO 01/15711 A1 | | 3/2001 | |
| WO | WO 01/24842 A2 | | 4/2001 | |
| WO | WO 01/91816 A1 | | 12/2001 | |

OTHER PUBLICATIONS

J. Bonadio et al.: "Gene Therapy for Tissue Repair and Regeneration," Advanced Drug Delivery Reviews, 1998, vol. 33, No. 1-2, pp. 53-69.

J. Bonadio et al.: "Localized, Direct Plasmid Gene Delivery in vivo: Prolonged Therapy Results in Reproducible Tissue Regeneration," 1999, Nature Medicine, vol. 5, No. 7, pp. 753-759.

S. Goldstein et al.: "Potential Role for Direct Gene Transfer in the Enhancement of Fracture Healing," Clinical Orthopedics and Related Research, 1998, vol. 355, Suppl., pp. S154-S162.

T. Ochiya et al.: "Biomaterials for Gene Deliver: Atelocollagen-mediated Controlled Release of Molecular Medicine," Current Gene Therapy, 2001, vol. 1, No. 1, pp. 31-52.

"Bio-Gide: Resorbable Bilayer Membrane for Bone Regeneration" Geistlich Biomaterials, 2 pp., 2010.

Breinan et al., "Reparative Tissues in Articular Cartilage Defects in a Canne Model Treated by Microfracture" 45th Annual Meeting, Orthoped. Res. Soc., Anaheim, CA. (one page), 1999.

Cai et al., "Lapine and Canine Bone Marrow Stromal Cells Contain Smooth Muscle Actin and Contract a Collagen-Glycosaminoglycan Matrix" Tissue Eng. 7(6):829-841, 2001.

Chondro-Gide: Collagen Membrane for Articular Cartilage Repair Geistlich Biomaterials, 15 pages, 2010.

Genzyme Tissue Repair, "CARTICEL™ (autologous cultured chondrocytes), Engineering a Better Repair" Genzyme Tissue Repair, 64 Sidney Street, Cambridge, MA 02139-4136, brochure (9 pages), 1997.

Greca et al., "Evaluation of Porcine Small Intestinal Submucosa in Achilles Tendon Repair" J. Appl. Res. 5(1):115-123, 2005.

Lee et al., "Harvest and Selected Cartilage Repair Procedures Affect Mechanical and Biochemical Properties of Uninvolved Articular Cartilage in the Canine Knee" 45th Annual Meeting, Orthoped. Res. Soc., Anaheim, CA (one page), 1999.

Lee et al., "The Contractile Behavior of Articular Chondrocytes in Collagen Matrices In Vitro" Tissue Eng. Soc., Orlando, Fla. (one page), 1998.

Mason et al., "Cartilage and bone regeneration using enhanced tissue engineering" Viral Vector Laboratory, NSUH, CORR 379S:S171-S178, 2000.

Menard et al., "Contractile Behavior of Smooth Muscle Actin-Containing Osteoblasts in Collagen-Gag Matrices In Vitro: Implant-Related Cell Contraction" Biomat., 21:1867-1877, 2000.

Mueller et al., "Alpha Smooth Muscle Actin in Bovine Meniscus Cells Seeded in Type I and Type II Collagen-Gag Matrices" 44th Annual Meeting Orthoped. Res. Soc., New Orleans, Louisiana, (one page), 1998.

Mueller et al., "α-Smooth Muscle Actin and Contractile Behavior of Bovine Meniscus Cells Seeded in Type I and Type II Collagen-Gag Matrices" J. Biomed. Mat. Res., 45:1-10, 1999.

Mutter et al., "Biomaterial Supports for Colonic Wall Defect Healing" Biomat. 17:1411-1415, 1996.

Nehrer et al., "Chondrocyte-Seeded Type I and Type II Collagen Implants Investigated In Vitro" Fifth World Biomaterials Congress, Toronto, CA (one page), 1996.

Nehrer et al., "Canine Chondrocytes Seeded in Type I and Type II Collagen Implants Investigated In Vitro" J. Biomed. Mater. Res. (Appl. Biomat.) 38:95-104, 1997.

Nehrer et al., "Chondorocyte-Seeded Type I and Type II Collagen Matrices Implanted in a Chondral Defect in a Canine Model" 7th Conference European Orthoped. Res. Soc., Barcelona. (one page), 1997.

(56) References Cited

OTHER PUBLICATIONS

Nehrer et al., "Matrix Collagen Type and Pore Size Influence Behaviour of Seeded Canine Chondrocytes" Biomat. 18:769-776, 1997.

Nehrer et al., "Autologous Chondrocyte-Seeded Type I and II Collagen Matrices Implanted in a Chondral Defect in a Canine Model" 44th Annual Meeting, Orthoped. Res. Soc., New Orleans, Louisiana, (one page), 1998.

Nehrer et al., "Characteristics of Articular Chondrocytes Seeded in Collagen Matrices In Vitro" Tissue Eng. 4(2):175-183, 1998.

Pieper et al., "Development of Tailor-Made Collagen-Glycosaminoglycan Matrices: Edc/Nhs Crosslinking, and Ultrastructural Aspects" Biomat. 21:581-593, 2000.

Schneider et al., "Expression of -Smooth Muscle Actin in Canine Intervertebral Disc Cells In Situ and in Collagen-Gag Matrices In Vitro" J. Orthoped. Res. 17(2):192-199, 1999.

Schulz-Torres et al., "Tendon Cell Contraction of Collagen-Gag Matrices In Vitro: Effect of Cross-Linking" Soc. for Biomat., Providence, R.I. (one page), 1999.

Stone et al., "Regeneration of Meniscal Cartilage with use of a Collagen Scaffold", J. Bone and Joint Sur. 79-A(12):1770-1777, 1997.

* cited by examiner

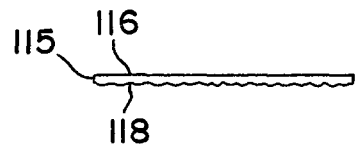
FIG. 3  FIG. 4
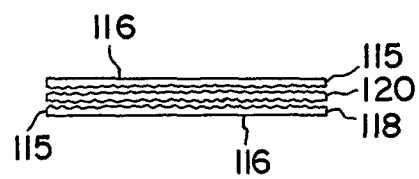
FIG. 4A
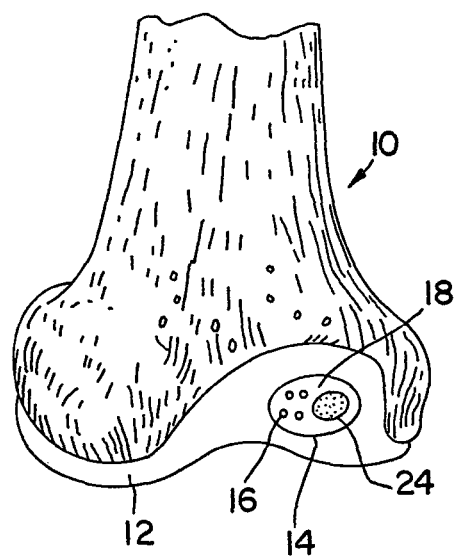
FIG. 5

COLLAGEN CARRIER OF THERAPEUTIC GENETIC MATERIAL AND METHOD

CROSS-REFERENCE TO RELATED APPLICATIONS

The present application is a continuation of U.S. application Ser. No. 11/046,897, filed Feb. 1, 2005, which is a continuation-in-part of U.S. application Ser. No. 10/213,437, filed Aug. 7, 2002, which claims the benefit of U.S. Provisional Application Ser. No. 60/311,078, filed Aug. 10, 2001. U.S. application Ser. No. 11/046,897 also is a continuation-in-part of U.S. application Ser. No. 09/925,728, filed Aug. 10, 2001, which claims the benefit of U.S. Provisional Application Ser. No. 60/224,010 filed Aug. 10, 2000. U.S. application Ser. No. 09/925,728 is a continuation-in-part of U.S. application Ser. No. 09/545,465, filed Apr. 7, 2000. U.S. application Ser. No. 11/046,897 also is a continuation-in-part of U.S. application Ser. No. 10/869,909, filed Jun. 18, 2004, which is a continuation of U.S. application Ser. No. 09/545,465, filed Apr. 7, 2000, now U.S. Pat. No. 6,752,834. U.S. application Ser. No. 09/545,465 is a continuation-in-part of International Application Serial No. PCT/GB98/02976, filed Oct. 5, 1998.

FIELD OF THE INVENTION

The present invention relates to the field of healing utilizing collagen material.

DESCRIPTION OF THE BACKGROUND ART

Collagen membranes have been utilized in the treatment of dental injuries (U.S. Pat. No. 5,837,278), spinal injuries (U.S. Pat. No. 6,221,109) and knee injuries (U.S. Pat. No. 6,352,558).

There remains a need in the art for improved methods of promoting healing utilizing collagen material.

SUMMARY OF THE INVENTION

In accordance with the present invention, a collagen matrix material is provided, which is charged with a cell growth-promoting derived nucleic acid sequence. The nucleic acid-charged collagen matrix material of the present invention may be utilized in methods of promoting healing.

BRIEF DESCRIPTION OF THE DRAWINGS

FIG. 3 is a side elevation schematic view showing a membrane for use in accordance with the present invention.

FIG. 4 is a side elevation schematic view showing a double-layer membrane for use in accordance with the present invention.

FIG. 4A is a side elevation schematic view showing a membrane for use in accordance with the present invention, including a collagen II inner layer matrix surrounded by barrier layers having opposite outer barrier faces.

FIG. 5 is a perspective view of the bone joint end member with portions broken away, showing subchondral puncturing and a bone mineral implant in accordance with another embodiment of the present invention.

DETAILED DESCRIPTION OF THE INVENTION

The present invention provides a collagen matrix material charged with (i.e., carrying) a cell growth-promoting derived nucleic acid sequence, preferably an isolated or purified nucleic acid sequence. The sequence can be a DNA sequence or an RNA sequence. In particularly preferred embodiments, the collagen matrix material is charged with an isolated gene sequence, most preferably of DNA.

A derived nucleic acid sequence for use in accordance with the present invention may promote cartilage cell growth, bone cell growth, or both.

A derived nucleic acid sequence is one which is not in its natural cellular environment, i.e., the environment of the derived nucleic acid sequence is not as occurs in nature.

Purified therapeutic nucleic acid sequences for use in accordance with the present invention may be derived from any suitable source, and may be charged to the collagen matrix material so as to promote cell growth. In accordance with one embodiment, a retroviral vector, or any other suitable gene-carrying and gene-introducing mechanism, is utilized. For example, a retroviral vector may be utilized for stably introducing human bone morphogenic protein 7 (BMP-7) cDNA into mesenchymal stem cells.

Gene therapy in accordance with the present invention involves the delivery of therapeutic genes or other genetic material into cells and tissues.

The present invention provides methods for repair of bone or cartilage including meniscus tissue, and surface cartilage in joints such as knees, for treating vertebral injuries including damage to vertebral discs, and for treating dental injuries, maxilofacial bone and other orthopedic injuries.

The methods of the invention may be practiced by covering an area of injury or damage to be treated, with a genetically charged collagen membrane in accordance with the present invention, fixing the collagen membrane over the area to be treated, and allowing the area to heal.

According to one embodiment, the invention provides a method for repairing injuries and damage to surface cartilage in joints such as knees. In accordance with one embodiment, cartilage defects are removed from the injured area to be treated, for example, by scraping of calcified cartilage from the injured area.

Figure 1:
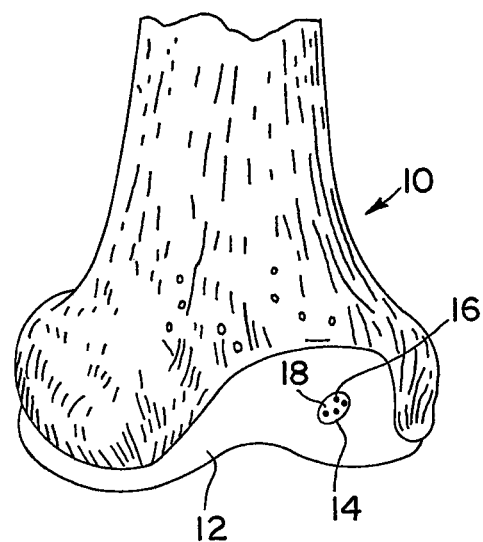
FIG. 1 is a perspective view with portions broken away showing an injured area of surface cartilage or meniscus of a bone joint end member.

After scraping of the calcified cartilage, a plurality of punctures may be formed in the subchondral plate of the area of injury utilizing a microfracture technique. FIG. 1 shows a bone 10 with cartilage 12 showing an area of injury 14 to be treated, wherein calcified cartilage has been scraped from the area to be treated. A plurality of punctures 16 have been formed in the subchondral plate 18 of the area of injury.

The punctures 16 in the subchondral plate can be formed, for example, with a straight pointed end of a microsurgical pick to a depth of, e.g., about 0.5-5 mm, more preferably about 1.5-2 mm. The punctures 16 may have a width of, for example, about 0.2-1.5 mm, more preferably about 0.5-1 mm, and most preferably about 0.8 mm.

Although the invention has been described with respect to utilization of the above-described microfracture technique involving forming a plurality of punctures in the subchondral plate, it is believed that the invention also is applicable to other methods of puncturing the subchondral plate, such as drilling, abrasion and the like.

After forming the punctures in the subchondral plate as described above, the punctures in the area to be treated can be covered by a patch 20 comprised of a multi-layer of collagen membrane material. The patch can be charged with extracellular cultivated chondrocytes, if desired.

Figure 2:
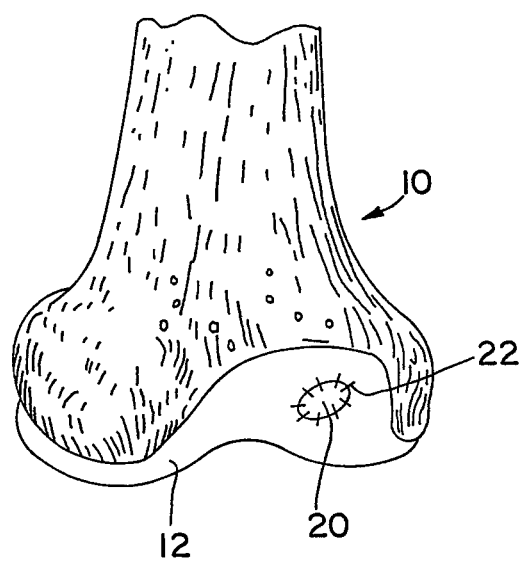
FIG. 2 is a perspective view with portions broken away showing the bone joint of FIG. 1 following covering the injured area with a patch made of a collagen membrane material in accordance with the present invention.

The patch then is fixed over the area to be treated, for example, by sutures 22 as shown in FIG. 2, to fix the patch to or over the healthy cartilage surrounding the area to be treated. Alternatively, the patch may be fixed over the area to be treated by adhesively bonding the patch to or over surrounding healthy cartilage, for example, utilizing an organic glue known in the art, or any other suitable method. The surgical procedure can be open surgery or arthroscopic surgery.

The patched area then is allowed to regenerate cartilage.

In accordance with one embodiment, the collagen membrane material is comprised of at least one barrier layer having at least one smooth face 116 so as to inhibit cell adhesion thereon and act as a barrier to prevent passage of cells therethrough. See FIG. 3. In accordance with this embodiment, the barrier layer further has a fibrous face 118 opposite the smooth face 116, the fibrous face allowing cell growth thereon. The smooth face 116 preferably is oriented away from the area to be treated, and the fibrous face 118 preferably is oriented toward the area to be treated. In preferred embodiments, the barrier layer is formed substantially or predominantly (i.e., greater than 50% by weight) of collagen I, collagen III or a mixture thereof. One suitable material is Biogide®, from Ed. Geistlich Söhne AG für Chemische Industrie, the assignee of the present invention. The Biogide® material is described in U.S. Pat. No. 5,837,278, incorporated herein by reference.

FIG. 4 shows a multi-layer membrane which may be used in accordance with the present invention. This membrane includes a barrier layer 115 as shown in FIG. 3, and further includes a matrix layer 120 formed substantially or predominantly of collagen II having an open sponge-like texture. A collagen membrane as shown in FIG. 4 is described in PCT Application No. PCT/GB98/02976, U.S. Ser. No. 09/545,465, filed Apr. 7, 2000, claiming priority from U.K. patent application no. 9721585.9, filed Oct. 10, 1997, incorporated herein by reference.

FIG. 4A shows another multi-layer membrane which may be used in accordance with the present invention. This membrane includes a pair of barrier layers 115 sandwiched around a central matrix layer 120 formed substantially or predominately of collagen II having an open sponge-like texture. In accordance with this embodiment, smooth faces 116 of the barrier layers are oriented outwardly, and fibrous faces 118 of barrier layers 115 are oriented inwardly toward matrix layer 120.

U.S. Ser. No. 08/894,517, filed Nov. 10, 1997 (corresponding to WO-A-96/25961), incorporated herein by reference, discloses a matrix based on collagen II which can be utilized according to the present invention. This membrane is formed substantially or predominantly (i.e., greater than 50% by weight) of collagen II.

The present invention also may utilize a matrix implant which will permit successful ingrowth of native chondrocytes and thus regeneration of cartilage tissue following implantation in vivo. Cartilage and ultimately new bone tissue can be reconstructed by the use of a collagen II matrix which in vivo is shielded not only from the surrounding connective tissue but also from the underlying bone or cartilage defect. This may be achieved through the use of a multi-layer membrane implant which itself is capable of preventing the undesired ingrowth of any surrounding tissues into the matrix, or which may be surgically implanted at the site of the defect so as to achieve this effect.

Viewed from one aspect the invention thus provides a multi-layer membrane comprising a matrix layer predominantly (i.e., greater than 50% by weight) of collagen II and having an open sponge-like texture, and at least one barrier layer having a close, relatively impermeable texture.

A particular advantage of the membrane according to the invention when used is that native cells are unable to penetrate or grow into the layer having a close, relatively impermeable texture.

While not wishing to be bound by theory, it is now believed that successful cartilage regeneration requires that the rapid ingrowth not only of native tissue cells, such as connective tissues, blood vessels etc., but also of any new bone tissue into the site of the defect be prevented. This may be achieved using a double-layer membrane in accordance with one embodiment of the invention which serves to shield the collagen matrix from the ingrowth of native tissue cells from one side. During surgical implantation this may be used in combination with a tissue graft, e.g. a periosteal graft, effective to prevent the ingrowth of native tissue cells from the opposing side. Thus, for example, a periosteal graft may initially be sutured in place such that this provides a covering over the bone or cartilage defect. A double-layer membrane of the invention may then be implanted at the site of the defect such that this lies in contact with the graft and may be arranged in such a way that the matrix layer faces toward the bone defect. Alternatively, a double-layer membrane of the invention is initially implanted at the site of the defect with the barrier layer facing toward the bone or cartilage defect. A periosteal graft may then be arranged such that this lies in contact with the matrix layer.

The graft may be adhered with a biocompatible adhesive such as fibrin glue, or pinned with resorbable polylactic pins, or if necessary or possible sutured in such a way that this then serves to provide an impermeable barrier to the ingrowth of any surrounding connective tissue.

In an alternative embodiment of the invention, the membrane itself may be effective to prevent the ingrowth of any native tissue cells. The invention may utilize a membrane comprising at least three layers in which a matrix layer being predominantly made from collagen II and having an open sponge-like texture is provided between two barrier layers having a close, relatively impermeable texture.

The matrix layer is capable of acting as a medium for the ingrowth of native chondrocytes thereby effecting regeneration of cartilage tissue. However, to further aid in regenerating cartilage tissue the matrix layer may be impregnated with chondrocytes either prior to or following implantation in vivo. While the matrix layer may be impregnated with chondrocytes immediately prior to implantation, e.g. by injection, it is expected that in general the chondrocytes will be introduced into the matrix layer by direct injection of a suspension of chondrocytes following implantation. In this way, chondrocytes present in the matrix layer of the membrane are able to effect regeneration of cartilage, and ultimately new bone, while the membrane at the same time prevents the ingrowth of other cell types from the surrounding tissues.

Chondrocytes for use in the invention may be obtained from cell sources which include allogenic or autogenic cells isolated-from articular cartilage, periosteum and perichondrium, and mesenchymal (stromal) stem cells from bone marrow. Since allogenic cells carry the potential for immune response and infectious complications, it is preferable to isolate the chondrocytes from autogenic cells, especially from autogenic articular cartilage. Techniques for harvesting cells are known and include enzymatic digestion or outgrowth culture. The harvested cells are then expanded in cell culture prior to reintroduction to the body. In general, at least 106, preferably at least 107 cells should be impregnated into the matrix layer to provide for optimal regeneration of cartilage tissue.

In general, it is desirable for the matrix layer of the membrane according to the invention to contain glycosaminoglycans (GAGs) such as hyaluronic acid, chondroitin 6-sulphate, keratin sulphate, dermatan sulphate etc. which serve to provide a natural medium in which chondrocytes can become embedded and grow. While it is possible to incorporate into the collagen matrix glycosaminoglycans from different sources which do not necessarily have the same composition, molecular weight and physiological properties as those from cartilage, preferred glycosaminoglycans are those extracted from cartilage itself. In general, the matrix layer preferably contains about 1 to 10 wt % of glycosaminoglycans, for example about 2 to 6 wt %. Although some glycosaminoglycans may be present in the impermeable layer, the greater part will be present in the matrix layer.

In native collagen tissues GAGs occur, at least in part, as a component of proteoglycans (PGs). The use of GAGs in the form of PGs is undesirable in view of potential immunological problems which can be caused by the protein content of the PGs. Preferably, the matrix layer is thus substantially free from any proteoglycans. Conveniently, this may be achieved by preparing the matrix layer from a mixture of a purified telopeptide-free collagen II material and glycosaminoglycans.

Other additives which may also be present in the matrix layer include, for example, chondronectin, laminin, fibronectin, calcium alginate or anchorin II to assist attachment of the chondrocytes to the collagen II fibers, bone and cartilage cell growth-promoting hormones, and growth factors such as cartilage inducing factor (CIP), insulin-like growth factor (IGF), transforming growth factor β (TGFβ) present as homodimers or heterodimers, osteogenic protein-1 (OP-1) and bone morphogenetic factors (BMPs) such as native or recombinant human BMP-2, BMP-3 (osteogenin), BMP-4, BMP-7, BMP-8, bFGF, CDMP or other skeletal matrix molecules, as well as signaling peptides such as transforming growth factor β (TGF-β, TGF-β1), vascular endothelial growth factor (EGF/VEGF), insulin-like growth factor (IGF/IGF-1), parathyroid hormone related protein (PTHrP) and platelet derived growth factor (PDGF). Nucleic acid sequences coding for the above, or which are capable of inducing or promoting in vivo production of the above, may be incorporated into the collagen matrix material of the present invention.

The product used in the invention also may act as a carrier for stem cells committed to a particular line of differentiation such as articular cartilage or bone. Such stem cells may be grown in vitro to increase their numbers, and applied to the repair sites in the carrier matrices with or without growth factors. Examples include mesenchymal stem cells and bone marrow stromal cells. Nucleic acid sequences coding for the above, or which are capable of inducing or promoting in vivo production of the above, may be incorporated into the collagen matrix material of the present invention.

BMP-2 affects the two pathways of bone formation independently—the direct formation of bone as well as the formation of cartilage which is then removed and replaced by bone. Composites of BMPs and collagen including bone matrix obtained by extraction from cortical bone from various sources or demineralized bone matrix comprise about 90% collagen and about 10% non-collagenous proteins (NCP) for BMP activity or for BMP/NCP induced chondrogenesis. Bone matrix-insoluble collagenous matrix and laminin or fibronectin act as carriers for BMPs. Some growth factors may also be present in the impermeable layer. However, preferably the greater part will be present in the matrix layer. In general, the membrane contains from about 100 µg to about 5 mg of growth factors. Nucleic acid sequences coding for the above, or which are capable of inducing or promoting in vivo production of the above, may be incorporated into the collagen matrix material of the present invention. The matrix may be charged by coating or impregnating with a solution carrying the genetic material.

The present invention may comprise a gene or nucleic acid-supplemented collagen matrix with cell growth-promoting genetic material or DNA incorporated therein. The collagen matrix material may provide for prolonged release of the cell growth-promoting genetic material. Upon release from the matrix into the body, the genetic material may transform cells in the body so as to promote cell growth and healing.

As indicated above, the membrane may comprise at least two layers having different structures. Preferably, the barrier layer of the membrane is predominantly made from collagen I and III. Alternatively, this may comprise a synthetic material, e.g. a synthetic resorbable polymer network optionally coated with a collagen material such as type I and/or type III collagen.

Examples of suitable synthetic materials include polyesters, polyglycolic and polylactic acids (PLA) homopolymers and copolymers, glycolide and lactide copolymers, polyorthoesters and polycaprolactones. Many examples of these are openly available, e.g. from Boehringer Ingelheim in their RESOMER range. PLA polymers as wax with an appropriate molecular size of ca. 650-1200 and not too rapid a degradation are preferred. A particularly preferred biodegradable polymer is poly(D,L-lactic acid) in which the ratio of D-lactide to L-lactide is approx. 70:30. An advantage of such synthetic materials is that these can have high mechanical stability which allows the membrane implant to be stretched over complex, three dimensional bone defects without tearing. Such materials are also suitable for suturing.

Advantageously, the barrier layer barrier layer structure is primarily made up of long collagen fibers which are so closely connected that high molecular substances cannot permeate this barrier. The long fibers provide high tensile strength and resistance to tearing so that the material is not only a good separation membrane but can also be readily sewn. It is often important in surgery that membrane implants can be sewn or pinned into position and many of the membranes which have previously been proposed do not provide this capability. A preferred membrane for use in accordance with the invention is mechanically stable enough to be handled surgically for implantation.

The matrix layer may be very porous and may have a specific weight as low as 0.02, which permits cells very rapidly to grow into this layer. This layer of the membrane, which may also contain glycosaminoglycans, may swell strongly and can take up as much as 5000% of liquid. Ideally, the matrix layer should provide a pore structure (pore volume fraction and pore size) which allows cell adhesion and growth and which permits the seeded cells to maintain the chondrocytic phenotype, characterized by synthesis of cartilage-specific proteins. Pore sizes will depend on the process (e.g., freeze drying) used to produce the collagen II matrix, but can be expected to be in the range of from about 10 to about 100 µm, e.g. 20 to 100 µm, e.g. about 85 µm. Such a pore size may readily be obtained by slow freezing at about −5 to −10° C. for about 24 hours followed by freeze-drying, or by adding ammonium bicarbonate to the slurry before lyophilization.

The matrix layer of the membrane is preferably provided by collagen II material obtained from cartilage, preferably hyaline cartilage from pigs.

While the desired thickness of the matrix layer will depend upon the nature of the bone or chondral defect to be treated, in general this can be expected to be in the range of from about 0.2 to about 12 mm, e.g. from about 1 to about 6 mm. The thickness of the barrier layer is preferably from about 0.2 to about 2 mm, e.g. from about 0.2 to about 0.7 mm. The final patch thickness may be about 20-120 mm, preferably about 60-100 mm.

The barrier layer may be provided by a natural animal membrane comprising collagen I and III. Being derived from a natural source, this is totally resorbable in the body and does not form toxic degradation products. Such membranes also have particularly high tear strength in either a wet or dry state and can therefore be surgically stitched if necessary. When moist the material is very elastic which allows this to be stretched over irregularly shaped bone defects.

Besides collagen, natural animal membranes contain many other biomaterials, which must be removed. It is known to treat such membranes with enzymes, solvents or other chemicals to effect purification and to use these membranes in medicine. Most of these materials are too thin and very often not particularly easy to use. The collagen fibrils have lost their native character and further disadvantages are that the material often has insufficient strength for use as a sewable material, has no water-swelling properties and provides no difference between the smooth grain side and the fibrous flesh side. The fibrous form of purified telopeptide-free collagen Type I or II, being less soluble and biodegradable, has been found to provide the most advantageous carrier material.

Membranes providing the barrier layer of the product according to the invention include peritoneum membrane from calves or pigs which retain their natural collagen structure. Peritoneum membranes from young pigs aged 6-7 weeks old (weighing 60-80 kg) are especially preferred.

The barrier layer should preferably comprise pure, native (not denatured) insoluble collagen and may be prepared in accordance with the method described in U.S. Pat. No. 6,837,278 (corresponding to WO-A-95/18638). The natural membrane may thus first be treated with alkali, for example aqueous NaOH at a concentration of about 0.2-4% by weight. This serves to saponify any fats and also proteins which are sensitive to alkali. The second step is the treatment of the material with an acid, usually an inorganic acid such as HCl. This eliminates acid-sensitive contaminants. The material is subsequently washed until the pH is in the range about 2.5-3.5. The membrane then has a smooth or grain side and a looser more fibrous side. It may be beneficial to effect some cross-linking of the membrane by heating to 100-120° C.

The collagen II material used to provide the matrix layer of the membrane can be obtained from cartilage by a similar procedure to that described above in relation to the barrier layer comprising predominantly collagen I and III. It is preferable to remove water from the cartilage by treatment with acetone followed by extraction of fat with a hydrocarbon solvent such as n-hexane, though alkanols such as ethanole, ethers such as diethyl ether or chlorinated hydrocarbons such as chloroform, or mixtures thereof may be used. The defatted material is then subjected to treatment with alkali which saponifies any residual fat and degrades some of the proteins present. Finally, the material is treated with acid which effects further protein degradation. The material is allowed to swell in water and is passed through a colloid mill to produce a slurry.

To produce the multi-layer membrane, the soft slurry containing collagen II is applied to the fibrous side of the smooth membrane prepared, for example in accordance with U.S. Pat. No. 5,837,278. Normally, the membrane will be placed on a smooth surface with the grain side down so that the collagen II slurry can readily be applied, e.g. by rubbing into the fibrous side of the membrane. The slurry thus forms a layer of any desired thickness which firmly adheres to the collagen membrane. The double-layer so formed is then subjected to freezing and freeze-drying to provide the desired sponge-like structure having a desired pore size. If necessary, some of the matrix layer may be removed to provide a double-membrane of uniform thickness. To produce a three-layer membrane, a second smooth membrane is then placed on top of the matrix layer with its fibrous side in contact with the matrix layer.

The collagen II slurry to be applied to the membrane in general contains about 1.0-4.0 weight % of the collagen, advantageously about 2-3 weight %. Conveniently, the pH value of this mixture should be adjusted to about 2.5-4.5, advantageously about 3.0-4.0.

The collagen II material further may be cross-linked after the freeze-drying step to stabilize the matrix layer. This also serves to increase the mechanical stability of the matrix layer and to reduce its rate of resorption by the body. Ideally, the degree of cross-linking should be such that the rate of degradation of the matrix matches the rate of tissue regeneration. Physically, cross-linking may be carried out by heating, but this must be effected carefully to avoid undesired loss of resorbability. Heating to temperatures of 100-120° C. for a period of from about 30 minutes to about 5 hours is preferable. More preferably, cross-linking may be effected by UV irradiation using a UV lamp, e.g. for a period of up to 8 hours. Cross-linking may also be carried out by chemical crosslinking with aldehydes, (e.g., formaldehyde, glyoxal, glutaraldehyde, or starchaldehyde, or the like), diisocyanates (e.g., hexamethylenediisocyanate), carbodiimides (e.g., [1-ethyl-3(3-dimethyl aminopropyl)carbodiimide]-hydrochloride (EDC)), or succinimides (e.g., N-hydroxysuccinimide (NHS)).

The collagen II material advantageously contains glycosaminoglycans (GAGs). The latter actually reacts with the collagen II to effect some cross-linking and produces an insoluble product. If necessary, further cross-linking can be effected by heating the material or by UV irradiation as discussed above. The reaction between the glycosaminoglycans and the collagen can be effected at ambient temperatures at a pH in the range 2.5-3.5. The quantity of glycosaminoglycan may be between about 1 and about 10% by weight. The material may be subjected to freezing and freeze-drying immediately after such treatment.

For example, GAGs such as chondroitin sulphate (CS) may be covalently attached to the collagen matrix using 1-ethyl-3-(3-dimethyl aminopropyl)carbodiimide (EDC) and N-hydroxysuccinimide (NHS) utilizing known methods. EDC/NHS crosslinking may be utilized for immobilizing GAGs with collagen matrices, which may include dermatan sulphate, heparin and heparan sulphate, as well as CS as indicated above. Such GAGs may be carried by a patch in accordance with the present invention so as to facilitate healing.

Slurry formation may be effected by raising the pH of the collagen II mass. In this procedure, the mass is cooled to about 4° C. and the pH value slowly raised by addition of cold aqueous NaOH at 4° C. up to a pH value about 6.5-7.5. Subsequently, the mass is held at ambient temperature for about 15-25 hours. In this time, the slurry is formed and after slurry formation, the mass can be frozen and freeze-dried.

A still further alternative is to neutralize the collagen II mass to a pH value about 6.8-7.4, subsequent to removal of air. The mixture is placed in the mold and incubated for about 15-20 hours at 37° C. A fine slurry develops which can subsequently be frozen and freeze-dried.

Which of the above methods is used depends upon the properties of the desired product. The first process gives the most stable product. However, the precipitation may give clumps of material and must be very carefully carried out. The second method gives a soft and uniform product which is, however, more soluble than the product of the first process.

In the production of the slurry, it is possible to additionally introduce further desirable substances such as medicines, e.g. antibacterials such as taurolidine and/or taurultam or antibiotics such as gentamycin.

After the application of the slurry to the membrane, the material is frozen. In order to obtain a reproducible pore size, the freezing must be carefully controlled and the rate and time of freezing, the pH value and the particle size must be accurately controlled. In order to obtain very small pores, the material may be shock frozen at very low temperature.

The frozen membrane is then freeze-dried and subsequently heated to about 110-130° C. In this way, some cross-linking is effected. Subsequently, the freeze-dried biomembrane may be adjusted to the required thickness so that the thickness of the matrix layer is commonly about 2 mm. The double membrane is then sterilized, for example by gamma-irradiation or with ethyleneoxide. Sterilization by strong irradiation e.g. with 60 Co in doses of 25 kGy may deactivate the BMPs. In such circumstances, the sterile matrix may be impregnated with BMPs in sterile saline prior to implantation.

The membrane according to the invention can be used in medicine in the following ways:

As a material for guided tissue regeneration, cell growth is encouraged by the matrix layer. The barrier layer inhibits undesired cell growth.

As a material for the repair of chondral defects, i.e. lesions which do not penetrate the subchondral plate, and in the repair of osteochondral defects.

The invention also provides the use of a multi-layer collagen membrane as described above in guided-tissue regeneration. The collagen II content of the membrane is particularly suitable for regeneration of cartilage tissue but is also suitable for other tissue types.

Viewed from a further aspect the invention thus provides a membrane as hereinbefore described for use as a guided tissue regeneration implant.

The invention further provides a method of treating a bone or cartilage defect in the human or non-human animal body, said method comprising application of a membrane as hereinbefore described to the defect, said membrane being oriented such that the barrier layer prevents the ingrowth of undesirable tissue types into the area of bone or cartilage regeneration.

In accordance with another embodiment, involving more substantial injuries which include injuries to the underlying bone as well as to the surrounding surface cartilage of a joint, an implant material 24 such as resorbable bone mineral may be implanted into the bone injury within the area to be treated. See FIG. 5. The bone mineral may be charged with chondrocytes, if desired. Punctures 16 may be made in the subchondral plate area 18 to be treated, and thereafter, a collagen membrane patch can be fixed over the area to be treated as shown in FIG. 2.

One suitable implant material is Bio-Oss® from Ed. Geistlich Söhne AG Für Chemische Industrie, the assignee of the present invention. Bio-Oss® is described in U.S. Pat. Nos. 5,167,961 and 5,417,975, incorporated herein by reference. Another suitable implant material is Bio-Oss Collagen® from Ed. Geistlich Söhne AG Für Chemische Industrie, which is resorbable bone mineral in a collagen matrix. Bio-Oss Collagen® is described in U.S. Pat. No. 5,573,771, incorporated herein by reference.

The bone mineral may be charged with any of the additives, growth factors and the like which are listed above in connection with charging of the collagen matrix.

There are numerous spinal surgeries performed each year to treat disc injuries, repair, remove or fuse vertebrae, or combinations thereof. During such surgeries, it is desirable to protect the spinal cord and the dura sheath surrounding the spinal cord from injury. Spinal surgeries often also involve insert of bone graft material to repair or replace damaged vertebrae. During the subsequent healing process, it is desirable to protect the spinal area from ingrowth of connective tissue and undesired cells which might interfere with proper healing.

The present invention also provides a method of protecting and healing areas of the spinal chord and column during and after spinal surgery or injury.

Figure 6:
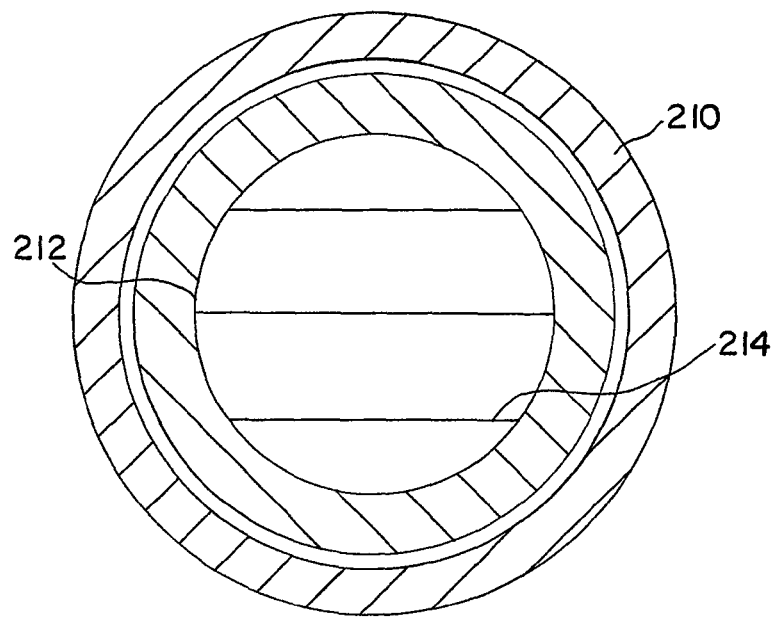
FIG. 6 is a sectional schematic view showing a spinal chord surrounded by a sheet of collagen membrane material in accordance with one embodiment of the present invention.

In accordance with one embodiment, during spinal surgery in which the dura sheath surrounding the spinal chord is exposed, a sheet of genetically charged collagen membrane material 210 is positioned adjacent the dura sheath 212 surrounding a patients spinal chord 214 so as to protect the dura sheath 212. See FIGS. 6 and 7.

Referring back to FIG. 7, in accordance with another embodiment of the present invention, a sheet 210' of collagen membrane material is positioned so as to surround at least a portion of a vertebrae 222 surrounding the spinal chord 214. In certain surgeries, a vertebrae implant material 224 such as resorbable bone mineral may be positioned between two vertebrae 222a and 222b so as to facilitate fusion of vertebrae 222a and 222b. In accordance with this aspect, the invention encompasses a sheet of collagen material 210' so as to surround at least a portion of the vertebrae implant material 224. One suitable vertebrae implant material is Bio-Oss® from Ed. Geistlich Söhne AG Für Chemische Industrie, the assignee of the present invention. Bio-Oss® is described in U.S. Pat. Nos. 5,167,961 and 5,417,975 incorporated herein by reference. Another suitable vertebrae implant material is Bio-Oss Collagen® from Ed. Geistlich Söhne AG Für Chemische Industrie, which is resorbable bone mineral in a collagen matrix. Bio-Oss Collagen® is described in U.S. Pat. No. 5,573,771 incorporated herein by reference. The present invention also is applicable to other bone graft methods, such as the "cage technique", in which a net of titanium enclosing bone graft material is inserted between vertebrae. In accordance with these embodiments, the sheet of collagen membrane material protects the implant material against ingrowth of connective tissue and other cells from outside adjacent bone material, which might interfere with osteocytes and other bone-regenerating cells from fully incorporating the spinal implant material into the spinal column for maximum strength and healing.

Figure 7:
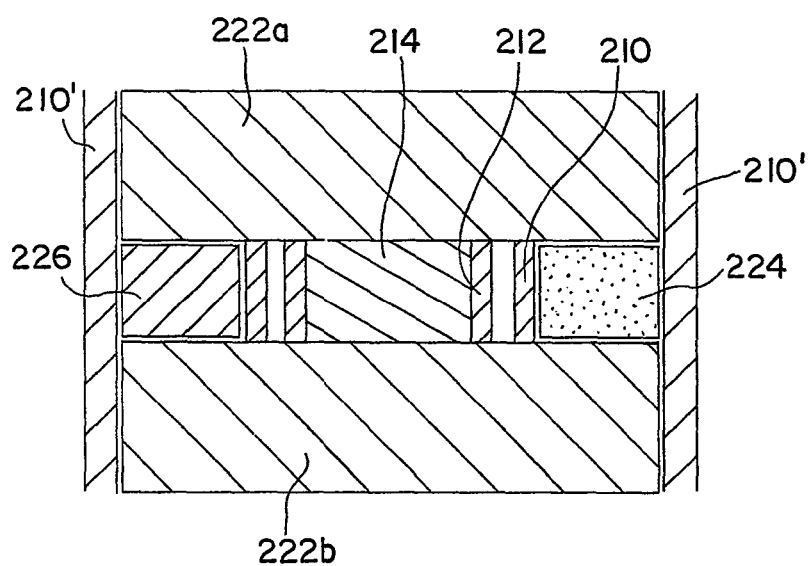
FIG. 7 is a schematic plan view in partial cross-section showing a second embodiment of the present invention wherein a first sheet of collagen membrane material is immediately adjacent a patients spinal chord, and a second sheet of collagen membrane material is positioned outside a patients vertebrae, spinal disc and inserted vertebrae implant material.

The method of the present invention also encompasses positioning a sheet of collagen membrane material 210' so as to surround at least a portion of a spinal disc 226 surrounding spinal chord 214 as shown in FIG. 7. In the embodiment shown in FIG. 7, the dura 212 has been surrounded by a genetically charged collagen membrane 210 in accordance with the present invention, and in addition thereto, a second genetically charged collagen membrane 210' has been wrapped around vertebrae 222a and 222b, as well as disc 226 and vertebrae implant material 24 for protection thereof. The present invention is thus capable of protecting the spinal chord dura from physical injury during surgery, and the barrier layer of membrane 210' protects the surgical site from ingrowth of unwanted cells during the healing process when membrane 210' is wrapped around the spinal column as shown in FIG. 7. The collagen membrane material 210, 210' is gradually resorbed into the patients body, avoiding any necessity of having to surgically remove the membranes after healing.

Figure 8:
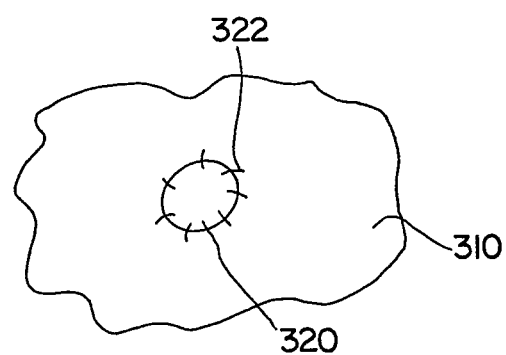
FIG. 8 is a side elevation schematic view showing a membrane for use in accordance with another embodiment of the present invention.

FIG. 8 shows utilization of the invention for repairing injury or damage to bone and/or cartilage in an area 310 which is a dental area, maxilofacial bone area or other orthopedic area. The method involves covering the area to be treated with a genetically charged collagen matrix material 320 as described above, and fixing the material in place utilizing any suitable means such as sutures 322, adhesive or the like.

The invention is further illustrated by the following examples, which are not intended to be limiting.

Example 1

Porcine rinds are ground into 20 ml pieces, treated with excess acetone to a water content of less than 3% by weight, and the acetone is evaporated. The dehydrated material is treated with a excess of hexane to a fat content of lower than 2% by weight, after which the hexane is evaporated. The dry, defatted rinds are treated with excess of water to form a slurry having a collagen content of about 4-7% by weight.

The slurry is subjected to alkali treatment by adding sodium hydroxide to form a 4% sodium hydroxide solution for at least four hours at 20° C. with stirring. The slurry is then washed with water to a pH of 8.4, then subjected to acidic treatment by addition of hydrochloric acid to form a 3.2% hydrochloric acid solution. The acidic treatment is conducted for at least 2 hours at 20° C. with stirring. The slurry then is washed with water to a pH of 2.5.

Water is added to the treated rinds to form a mixture having a solid content of 1.5% by weight. The mixture is homogenized to a gel-like slurry. The gel-like slurry then is freeze-dried to form collagen I sponges.

Example 2

Porcine rinds are ground into 10 ml pieces, then dehydrated by air-drying in a 25° C. air flow to a residual water content lower than 15% by weight. The dehydrated material is defatted by treatment with an excess of methylene chloride/methanol (87%:13% by weight) to a fat content of lower than 2%. The solvents are then evaporated.

The dry, defatted rinds are treated with an excess of water to form a mixture having a collagen content of about 4-7% by weight.

The mixture then is subjected to alkali treatment by adding sodium hydroxide to form a 4% by weight sodium hydroxide solution, for at least four hours at 20° C. with stirring. The mixture then is washed with water to a pH of 8.4.

The mixture then is subjected to acidic treatment by addition of hydrochloric acid to form a 3.2% hydrochloric acid solution, for at least 2 hours at 20° C. with stirring. The mixture then is washed with water to a pH of 2.5.

Water is added to the treated rinds to form a mixture with a solid content of about 1.5% by weight, then homogenized to a gel-like slurry. The gel-like slurry is freeze-dried to form collagen I sponges.

Example 3

Porcine rinds are ground into 10 ml pieces, then dehydrated by air-drying in a 25° C. air flow to a residual water content of lower then 15% by weight.

The dehydrated rinds are subject to defatting by treatment with an excess of methylene chloride/methanole (87%:13% by weight) to a fat content of lower than 2%. The solvents then are evaporated.

The dry, defatted rinds are treated with an excess of water to form a mixture having a collagen content of about 4-7% by weight. If necessary, additional water is added to the treated rinds to form a mixture having a solids content of about 4% by weight and the mixture is homogenized into a gel-like dough.

10 kg of 4M guanidine hydrochloride solution is added per kg of gel-like dough to form a mixture which is shaken at 4° C. for 24 hours. The mixture then is extensively washed with water and the residual collagen is filtered.

The mixture then is subjected to pepsin digestion by adding pepsin to the mixture at a pepsin:collagen ratio of 1:10 weight/weight in 0.1M lactic acid at a pH of 2.5 for 48 hours at 4° C. with shaking, so as to dissolve the collagen. The pH of the mixture is increased to about 7 with 2M sodium hydroxide, and collagen is precipitated by adding sodium chloride to a final content of 0.7M. The precipitated collagen is collected by centrifugation. Water is added to the precipitate to form a gel-like dough having a solids content of about 2.5% by weight, and the gel-like dough is freeze-dried to form collagen I sponges.

Example 4

Deep frozen porcine cartilage is thawed over a period of 72 hours at 6° C. The thawed cartilage is ground to a size of about 3 mm. Water is added to the ground cartilage to form a mixture having a solids content of 4% by weight, and homogenized into a gel-like dough. 10 kg 4M guanidine hydrochloride solution is added per kg dough, and shaken at 4° C. for 24 hours. The thus-treated material is extensively washed with water, and the residual collagen is filtered. To the filtered collagen is added pepsin at a pepsin:collagen ratio of 1:10 w/w and 0.1 M lactic acid to a pH of 2.5, and shaken at 4° C. for 48 hours so as to dissolve the collagen. The pH of the mixture is increased to about 7 with 2M sodium hydroxide, and collagen is precipitated by adding sodium chloride to a final content of 0.7M. The precipitated collagen is collected by centrifugation, and sodium chloride is washed out at pH 7 with water.

A hydrochloric acid in water solution at pH 3.3 is added to the precipitate to achieve a solids content of 2.5% by weight, and stirred well at pH 3.3 to obtain a uniform gel-like dough. The gel-like dough is freeze-dried to form collagen II sponges.

Example 5

Deep frozen porcine cartilage is thawed over a 72 hour period at 6° C., and then ground into a size of about 5 mm. The ground material is treated with an excess of acetone to a water content of below 3% by weight. The acetone then is evaporated. The thus dehydrated material is treated with an excess of hexane to achieve a fat content of lower than about 2%, and the hexane is evaporated. The thus dried, defatted material is treated with an excess of water to obtain a mixture with a collagen content of about 5-12% by weight. This mixture is subjected to alkaline treatment with 4% sodium hydroxide solution for a period of 24 hours with stirring at 20° C., then washed with water to a pH of 9.3. The material then is subjected to acidic treatment with 3.2% hydrochloric acid for at least 2.5 hours at 20° C. with stirring. The material then is washed with water to a pH of 3.2.

Water then is added to the thus treated rinds to achieve a solids content of about 1.5% by weight, and homogenized to a gel-like slurry. The gel-like slurry is then freeze-dried into collagen II sponges.

Example 6

Preparation of Combined Collagen I and Collagen II Sponges

A collagen I gel-like slurry or gel-like dough produced as taught in Examples 1-3 (before freeze-drying) are mixed with a collagen II-containing gel-like dough or gel-like slurry produced as set forth in Examples 4-5 (before freeze-drying) in ratios of collagen I:II (w/w referenced to dry weight) of 1% collagen I:99% collagen II to 99% collagen I:1% collagen II, and freeze-dried into a collagen I/collagen II sponge.

Example 7

A collagen I 1.5% by weight slurry after homogenization (Example 1) and a collagen II 1.5% by weight slurry after homogenization (Example 5) are mixed in a ratio of 10:90% (w/w), then freeze-dried into a collagen I/collagen II sponge.

Example 8

Gel-like slurries or gel-like doughs produced in accordance with the Examples 1-7 are mixed with additives comprising glucosaminoglycans, proteoglycans or mixtures thereof, are added in amounts to achieve a 0.5-50% concentration by weight of the additive(s) on a dry weight basis.

Example 9

Dry sponge material as produced according to Examples 1-7 are treated with an aqueous solution of additives comprising glucosaminoglycans, proteoglycans or mixtures thereof, then freeze-dried to achieve an additive(s) content of 0.5-50% dry weight.

Example 10

Hyaluronic acid is dissolved in water to form a 5% solution by weight and the solution is mixed with a 1.5% collagen I gel-like slurry as prepared in Example 1 (prior to freeze-drying) and then freeze-dried to form a sponge having a final hyaluronic acid content of 10% by weight on a dry weight basis.

Example 11

Chondroitin-6-sulfate is dissolved in water to form a 1% by weight Chondroitin-6-sulfate solution, and added to a collagen II sponge as produced in Example 4, such that the collagen II sponge adsorbs the chondroitin-6-sulfate solution. The wet sponge then is freeze-dried again to a final content of Chondroitin-6-sulfate of 2% by weight on a dry weight basis.

Example 12

Sponges prepared as in Examples 1-11 are stabilized against enzymatic attack by crosslinking with ultraviolet (UV) radiation, dehydrothermal treatment (DHT), chemical crosslinking with aldehydes, (e.g., formaldehyde, glyoxal, glutaraldehyde, or starchaldehyde, or the like), diisocyanates (e.g., hexamethylenediisocyanate), carbodiimides (e.g., [1-ethyl-3(3-dimethyl aminopropyl)carbodiimide]-hydrochloride (EDC)), or succinimides (e.g., N-hydroxysuccinimide (NHS)).

Example 13

A collagen I (90%)-hyaluronic acid (10%) sponge as prepared in Example 10 is stabilized by UV crosslinking with a 57 microwatt/cm$^2$ UV radiation source at a distance of 50 cm from the sponge and an irradiation time of 120 minutes.

Example 14

A collagen I (88%)-hyaluronic acid (10%)-chondroitin-6-sulfate (2%) sponge prepared as in Example 9 is stabilized by EDC crosslinking by soaking 50 mg sponge (dry weight) in 20 ml 40% igen (v/v) ethanole, buffered at pH 5.5, containing 33 m EDC, for a reaction period of 4 hours at a temperature of 20° C. Reaction products are removed by washing and the material then is freeze-dried.

Example 15

Hyaluronic acid is dissolved in water to form a 5% by weight hyaluronic acid solution, which then is mixed with a 1.5% collagen II gel-like slurry as prepared in Example 5 before homogenization. The material then is homogenized as in Example 5 and freeze-dried to form a sponge having a hyaluronic acid content of 10% by weight on a dry weight basis. The sponge then is stabilized by UV crosslinking utilizing the same radiation source as in Example 13, but at a distance from the sponge of 65 cm for a duration of 200 minutes.

Example 16

Chondroitin-6-sulphate is dissolved in water to form a 2.7% by weight chondroitin-6-sulfate solution. This solution is mixed with a 2.5% by weight collagen II gel-like dough as prepared in Example 4, before freeze-drying. The material is then freeze-dried to form a sponge containing chondroitin-6-sulphate 2.8% by weight on a dry weight basis. The sponge then is stabilized by EDC/NHS crosslinking by soaking 50 mg sponge (dry weight) in 20 ml 40% igen (v/v) ethanole, buffered at pH 5.5 (wherein one liter of the ethanole contains 33 mmol EDC and 20 mmol NHS). The reaction time is 4 hours at 22° C., and reaction products then are removed by washing. The material then is freeze-dried.

Example 17

A collagen I/II (10:90 w/w) sponge as prepared in Example 7 is redispersed in pH 3.0 hydrochloric acid solution with a blender to a solids content of 2% by weight. Hyaluronic acid is dissolved in water to a 3% by weight solution and chondroitin-6-sulfate is dissolved in water to a 0.9% by weight solution. The hyaluronic acid and chondroitin-6-sulfate solutions are mixed with the 2% by weight collagen I/II dispersion, and freeze-dried to a final content of hyaluronic acid of 10% by weight, and a final content of chondroitin-6-sulfate of 2.75% by weight, on a dry weight basis. The freeze-dried sponge then is stabilized by EDC/NHS crosslinking by soaking 50 mg of the sponge (dry weight) in 20 ml 40% igen (v/v) ethanole, buffered at pH 5.5 (wherein one liter of the ethanole contains 33 mmol EDC and 20 mmol NHS) for a reaction period of 4 hours at a temperature of 22° C. Reaction products are removed by washing and the mass is freeze-dried.

Since many modifications, variations and changes in detail may be made to the described embodiments, it is intended that all matter in the foregoing description and shown in the accompanying drawings be interpreted as illustrative and not in a limiting sense.

The invention claimed is:

1. A nucleic acid carrier collagen material consisting of a membrane sheet having a thickness of about 0.2-2 mm, wherein said membrane sheet is formed from natural animal membrane comprising native insoluble collagen I, collagen III or a mixture thereof, wherein said membrane sheet carries a nucleic acid sequence encoding a protein that promotes cell growth, wherein said membrane sheet includes a barrier layer which acts as a barrier to inhibit passage of cells therethrough, wherein said barrier layer has a smooth face so as to inhibit cell adhesion thereon, and wherein said barrier layer further has a fibrous face opposite said smooth face.

2. The collagen material of claim 1, wherein said membrane is formed from peritoneum, and has a thickness of about 0.2-0.7 mm.

3. The collagen material of claim 1 wherein said nucleic acid sequence is purified from its natural cellular environment.

4. The collagen material of claim 1 wherein said nucleic acid sequence is a gene.

5. The collagen material of claim 1 wherein said nucleic acid sequence is DNA.

6. The collagen material of claim 1 wherein said protein promotes cartilage growth.

7. The collagen material of claim 1 wherein said protein promotes bone growth.

8. A method of promoting regeneration of surface cartilage of a joint, comprising covering an area of damaged cartilage of a joint with a collagen material according to claim 1; fixing said collagen material over said area; and allowing said area to regenerate cartilage.

9. A method of repairing injury or damage to bone, cartilage or a combination thereof, comprising covering an area of injured or damaged bone, cartilage or a combination thereof with a collagen material according to claim 1; fixing said collagen material over said area; and allowing said area to heal.

10. The method of claim 9 wherein said area is a dental area, maxilofacial area or spinal area.

11. The method of claim 9 further comprising, prior to covering said area, removing a cartilage defect from said area.

12. The method of claim 9, further comprising, prior to said covering, making a plurality of punctures to a subchondral plate of said area.

* * * * *